(12) United States Patent
Kase et al.

(10) Patent No.: US 9,768,444 B2
(45) Date of Patent: Sep. 19, 2017

(54) COATED NICKEL HYDROXIDE POWDER FOR POSITIVE ELECTRODE ACTIVE MATERIAL OF ALKALINE SECONDARY BATTERY, AND EVALUATION METHOD FOR COATING ADHESION PROPERTIES OF COATED NICKEL HYDROXIDE POWDER

(71) Applicant: SUMITOMO METAL MINING CO., LTD., Tokyo (JP)

(72) Inventors: Katsuya Kase, Ehime (JP); Ryuichi Kuzuo, Ehime (JP); Minoru Shiraoka, Ehime (JP); Hideo Sasaoka, Ehime (JP)

(73) Assignee: Sumitomo Metal Mining Co., Ltd., Tokyo (JP)

( * ) Notice: Subject to any disclaimer, the term of this patent is extended or adjusted under 35 U.S.C. 154(b) by 0 days.

(21) Appl. No.: 14/438,527

(22) PCT Filed: Oct. 12, 2013

(86) PCT No.: PCT/JP2013/077866
§ 371 (c)(1),
(2) Date: Apr. 24, 2015

(87) PCT Pub. No.: WO2014/065145
PCT Pub. Date: May 1, 2014

(65) Prior Publication Data
US 2015/0295231 A1    Oct. 15, 2015

(30) Foreign Application Priority Data

Oct. 25, 2012 (JP) ................. 2012-235467
Feb. 28, 2013 (JP) ................. 2013-038331

(51) Int. Cl.
| | |
|---|---|
| H01M 4/36 | (2006.01) |
| H01M 10/30 | (2006.01) |
| G01N 21/59 | (2006.01) |
| H01M 4/52 | (2010.01) |
| H01M 4/26 | (2006.01) |
| H01M 4/32 | (2006.01) |
| G01N 19/04 | (2006.01) |

(52) U.S. Cl.
CPC ............ *H01M 4/366* (2013.01); *G01N 21/59* (2013.01); *H01M 4/26* (2013.01); *H01M 4/32* (2013.01); *H01M 4/52* (2013.01); *H01M 10/30* (2013.01); *G01N 19/04* (2013.01); *G01N 2201/022* (2013.01); *G01N 2203/0284* (2013.01); *G01N 2203/0641* (2013.01); *H01M 2220/30* (2013.01)

(58) Field of Classification Search
CPC .......... G01N 19/04; G01N 2033/0091; G01N 2033/0096; G01N 21/59; G01N 2201/022; G01N 2203/0284; G01N 2203/0641; H01M 10/30; H01M 2220/30; H01M 4/366; H01M 4/52
See application file for complete search history.

(56) References Cited

U.S. PATENT DOCUMENTS

| | | | | |
|---|---|---|---|---|
| 6,706,442 | B1 * | 3/2004 | Sakamoto | ............ B82Y 30/00 429/218.1 |
| 8,603,677 | B2 * | 12/2013 | Kuzuo | ................. H01M 4/366 427/77 |
| 2015/0280224 | A1 * | 10/2015 | Kase | ..................... H01M 4/52 429/218.2 |

FOREIGN PATENT DOCUMENTS

| | | | |
|---|---|---|---|
| CN | 101106193 | | 7/2007 |
| CN | 101332509 A | * | 12/2008 |
| JP | 63152866 | | 6/1988 |
| JP | 7133115 | | 5/1995 |
| JP | 2000077070 | | 3/2000 |
| JP | 2000149941 | | 5/2000 |
| JP | 2002029755 | | 1/2002 |
| JP | 2002175804 | | 6/2002 |
| JP | 2003151545 A | * | 5/2003 |

OTHER PUBLICATIONS

English Abstract of JP 63152866.
English Abstract of JP 7133115.
English Abstract of JP 2000149941.
English Abstract of JP 2000077070.
English Abstract of JP 2002175804.
English Abstract of JP 2002029755.
English Abstract of CN101106193.

* cited by examiner

*Primary Examiner* — Carlos Barcena
(74) *Attorney, Agent, or Firm* — Dykema Gossett PLLC

(57) ABSTRACT

A coated nickel hydroxide powder that has a cobalt compound coating having improved uniformity and adhesion properties on the surface of particles thereof and is therefore suitable for a positive electrode active material of an alkaline secondary battery is obtained by coating the surface of nickel hydroxide particles with a cobalt compound, and has a transmittance ratio of 30% or higher as determined by $(A-B_{max})/(B_0-B_{max})$. The transmittance A (coated nickel hydroxide powder), the transmittance $B_0$ (nickel hydroxide powder), or the transmittance $B_{max}$ (nickel hydroxide powder and cobalt compound containing cobalt in an amount corresponding to the amount of cobalt contained in the coating) can be determined by measuring the transmittance of a tubular transparent cell after shaking the tightly-closed transparent cell containing each powder for a certain time and then taking the contents out of the transparent cell.

14 Claims, 3 Drawing Sheets

COATED NICKEL HYDROXIDE POWDER FOR POSITIVE ELECTRODE ACTIVE MATERIAL OF ALKALINE SECONDARY BATTERY, AND EVALUATION METHOD FOR COATING ADHESION PROPERTIES OF COATED NICKEL HYDROXIDE POWDER

TECHNICAL FIELD

The present invention relates to a coated nickel hydroxide powder for a positive electrode active material of alkaline secondary battery, which is coated with a cobalt compound to ensure conductivity between particles thereof and enhance the utilization ratio, lifetime characteristics, and output characteristics of a battery, and an evaluation method for the adhesion properties of the cobalt compound coating.

BACKGROUND ART

With recent development of portable devices, there has been a strong demand for higher-capacity secondary batteries for use in such devices. For example, a nickel hydroxide powder for a positive electrode material of alkaline secondary battery has been improved by forming a solid solution with cobalt to improve the utilization ratio of an alkaline secondary battery at high temperatures or by forming a solid solution with zinc or magnesium to improve the lifetime characteristics of an alkaline secondary battery.

Alkaline secondary batteries have come to be used as high-output power sources such as power sources for hybrid cars; therefore, there has been a strong demand not only for such improvement in utilization ratio at high temperatures or lifetime characteristics but also for improvement in output characteristics. However, a nickel hydroxide powder for a positive electrode active material of alkaline secondary battery is an electrical insulating material and poor in conductivity, which causes a problem that an electrical current does not sufficiently run through nickel hydroxide; therefore, the electrochemical availability of nickel hydroxide is low.

In order to solve such a problem, a cobalt compound such as cobalt oxide or cobalt hydroxide is added as a conductive material to ensure conductivity between nickel hydroxide particles. Such a cobalt compound added is dissolved in a high-concentration alkali metal hydroxide solution used as an electrolyte in an alkaline secondary battery, and is oxidized and deposited as cobalt oxyhydroxide on the surface of nickel hydroxide particles during electrical charge so that electrical conductivity is developed and a conductive network is formed between the nickel hydroxide particles.

A positive electrode of a nickel hydroxide powder having a cobalt compound added thereto is generally produced by the steps of mixing a nickel hydroxide powder, a cobalt compound powder, and a hinder to form a paste, filling the pores of a three-dimensional metal porous body, such as a foamed metal (made of nickel metal), with the paste, and subjecting the three-dimensional metal porous body to drying and pressing. However, the cobalt compound powder mixed together with the binder is not necessarily well dispersed in the nickel hydroxide powder. Therefore, the positive electrode has a problem that its utilization ratio is significantly reduced under the conditions of use during high-load electrical charge.

As a means for solving such a problem, a method has been proposed in which the surface of particles of a nickel hydroxide powder is coated with a cobalt compound. For example, Patent Literature 1 proposes a nickel active material for storage battery mainly comprising nickel hydroxide particles having a β-type cobalt hydroxide thin layer formed thereon. Patent Literature 1 states that this nickel active material is obtained by depositing a nickel hydroxide powder from a nickel salt in an aqueous alkali solution, immersing the nickel hydroxide powder in an aqueous solution of cobalt sulfate or cobalt nitrate, and neutralizing the aqueous solution with an aqueous alkali solution.

Further, Patent Literature 2 proposes a method for producing a nickel hydroxide powder coated with cobalt hydroxide, in which a cobalt-containing aqueous solution and an ammonium ion supplier are simultaneously, continuously, and quantitatively supplied to a nickel hydroxide powder-containing aqueous solution adjusted to pH 11 to 13 with a caustic alkali.

Further, Patent Literature 3 proposes a method in which a cobalt ion-containing aqueous solution, with a supply rate of 0.7 g/min or less in terms of cobalt per kilogram of the raw nickel hydroxide powder, and an ammonium ion-containing aqueous solution are supplied to a suspension of a raw nickel hydroxide powder to achieve a nickel ion concentration of 10 to 50 mg/l and a cobalt ion concentration of 5 to 40 mg/l while the pH, temperature, and ammonium ion concentration of the suspension are kept at predetermined values.

CITATION LIST

Patent Literatures

Patent Literature 1: JP 63-152866 A
Patent Literature 2: JP 7-133115 A
Patent Literature 3 JP 2000-149941 A

SUMMARY OF INVENTION

Technical Problem

All the above methods described in Patent Literatures 1 to 3 are intended to ensure the dispersibility and uniformity of a conductive cobalt compound by previously coating the surface of particles of a nickel hydroxide powder with cobalt hydroxide. However, such conventional methods have a problem that a cobalt hydroxide coating is non-uniformly formed on the surface of nickel hydroxide particles or is peeled off in the process of paste preparation; therefore, it is difficult to ensure the uniformity of a conductive cobalt compound.

Particularly, if the coating layer is peeled off in the process of paste preparation, there is a possibility that the density of the coating material in a resulting electrode plate varies from place to place; therefore, a conductive network between the nickel hydroxide particles is not uniformly formed so that the utilization ratio of the positive electrode is significantly reduced under the conditions of use during high load electrical charge. For this reason, it is important for the product evaluation of cobalt hydroxide-coated nickel hydroxide to evaluate the adhesiveness of cobalt hydroxide as a coating layer to previously know the peeling resistance of the coating layer in the process from paste preparation to the completion of electrode plate preparation.

In view of the circumstances, it is an object of the present invention to provide a method for simply and reliably evaluating the adhesion properties of a cobalt compound coating of a coated nickel hydroxide powder for a positive electrode active material of alkaline secondary battery, and a coated nickel hydroxide powder for a positive electrode active material of alkaline secondary battery whose cobalt compound coating has excellent uniformity and adhesion properties when evaluated by the method so that the cobalt compound coating can be inhibited from being peeled off in the process from paste preparation to completion of electrode plate preparation.

Solution to Problem

In order to achieve the above object, the present inventors have intensively studied the coating adhesion properties of a cobalt compound-coated nickel hydroxide powder, and as a result have found that coating adhesion properties can be evaluated by shaking a tubular transparent cell containing a coated nickel hydroxide powder and then measuring the transmittance of the cell. Further, the present inventors have found that when a transmittance ratio calculated from the transmittance is equal to or higher than a specific value, the cobalt compound coating of the coated nickel hydroxide powder has high adhesiveness and is therefore inhibited from being peeled off in the process of paste preparation so that the uniformity of a conductive cobalt compound in a positive electrode can be ensured. These findings have led to the completion of the present invention.

More specifically, the present invention is directed to a coated nickel hydroxide powder for a positive electrode active material of alkaline secondary battery, comprising nickel hydroxide particles having a coating made of a cobalt compound on a surface thereof, wherein when a transmittance A, a transmittance $B_0$, and a transmittance $B_{max}$ are defined as follows, a transmittance ratio (%) represented by $(A-B_{max})/(B_0-B_{max}) \times 100$ is 30% or higher, transmittance A: transmittance of a tubular transparent cell measured after shaking the tubular transparent cell containing the coated nickel hydroxide powder for a predetermined time and then taking the contents out of the tubular transparent cell;

transmittance $B_0$: transmittance of a tubular transparent cell measured after shaking the tubular transparent cell containing a nickel hydroxide powder for a predetermined time and then taking the contents out of the tubular transparent cell; and transmittance $B_{max}$: transmittance of a tubular transparent cell measured after shaking the tubular transparent cell, for a predetermined time, containing the nickel hydroxide powder and a cobalt compound powder containing cobalt in an amount corresponding to an amount of cobalt contained in the coating of the coated nickel hydroxide powder and then taking the contents out of the tubular transparent cell.

In the coated nickel hydroxide powder for a positive electrode active material of alkaline secondary battery according to the present invention, the cobalt compound constituting the coating preferably mainly contains cobalt oxyhydroxide or a mixture of cobalt oxyhydroxide and cobalt hydroxide, and an amount of cobalt contained in the cobalt compound constituting the coating is preferably 90 mass % or more of a total mass of metal elements in the coating. Further, an amount of cobalt contained in the cobalt compound that coats the surface of the particles is preferably 1 to 10 mass % of a total mass of the coated nickel hydroxide powder.

The present invention is directed also to an evaluation method for coating adhesion properties of a coated nickel hydroxide powder for a positive electrode active material of alkaline secondary battery comprising nickel hydroxide particles having a coating made of a cobalt compound on a surface thereof, the method comprising: measuring transmittances A, $B_0$, and $B_{max}$ defined as follows; and evaluating coating adhesion properties of a coated nickel hydroxide powder based on a transmittance ratio (%) represented by $(A-B_{max})/(B_0-B_{max}) \times 100$, transmittance A transmittance of a tubular transparent cell measured after shaking the tubular transparent cell containing the coated nickel hydroxide powder for a predetermined time and then taking the contents out of the tubular transparent cell;

transmittance $B_0$: transmittance of a tubular transparent cell measured after shaking the tubular transparent cell containing a nickel hydroxide powder for a predetermined time and then taking the contents out of the tubular transparent cell; and transmittance $B_{max}$: transmittance of a tubular transparent cell measured after shaking the tubular transparent cell, for a predetermined time, containing the nickel hydroxide powder and a cobalt compound powder containing cobalt in an amount corresponding to an amount of cobalt contained in the coating of the coated nickel hydroxide powder and then taking the contents out of the tubular transparent cell.

In the above evaluation method for coating adhesion properties of a coated nickel hydroxide powder according to the present invention, the tubular transparent cell is preferably a circular or rectangular cylindrical transparent cell, and is preferably made of quartz or hard glass. Further, the shaking of the tubular transparent cell is preferably performed by performing reciprocating movement in a direction parallel to a central axis of the cell or by performing the reciprocating movement simultaneously with rotational or semi-rotational movement around the central axis of the cell.

Advantageous Effects of Invention

According to the present invention, it is possible to easily evaluate the adhesion properties of a cobalt compound coating of a coated nickel hydroxide powder without preparing an electrode paste or an electrode plate or without using water or a solvent. Further, the coated nickel hydroxide powder according to the present invention has a uniform cobalt compound coating on the surface of particles thereof and is capable of preventing its coating from being peeled off in the process of preparing a paste by mixing with a binder or the like, and is therefore extremely excellent for a positive electrode active material of alkaline secondary battery.

Further, the coated nickel hydroxide powder according to the present invention is not only capable of preventing its coating made of cobalt hydroxide or cobalt oxyhydroxide from being peeled off during paste preparation but also has high conductivity, and is therefore suitable for use in a power source for electric car or hybrid car required to have high-output characteristics. Further, such improved conductivity increases the utilization ratio of a positive electrode; therefore, the coated nickel hydroxide powder according to the present invention is very effective for use also in a power source for portable electronic device required to have a high capacity.

DESCRIPTION OF EMBODIMENTS

Figure 1:
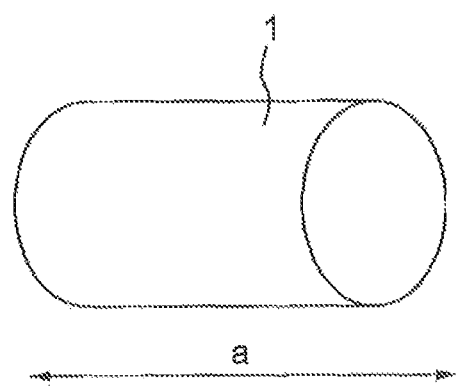
FIG. 1 A schematic diagram showing shaking by reciprocating movement in a direction parallel to the central axis of a tubular transparent cell.

First, an evaluation method for the adhesion properties of a cobalt compound coating of a coated nickel hydroxide powder according to the present invention will be described. The evaluation method for coating adhesion properties according to the present invention evaluates the coating adhesion properties of a coated nickel hydroxide powder for a positive electrode active material of alkaline secondary battery comprising nickel hydroxide particles having a coating made of a cobalt compound on a surface thereof, comprising: measuring transmittances A, $B_0$, and $B_{max}$ defined as follows; and evaluating the coating adhesion properties of a coated nickel hydroxide powder based on a transmittance ratio (%) calculated by $(A-B_{max})/(B_0-B_{max}) \times 100$.

<Definitions of Transmittances>

Transmittance A: Transmittance of a tubular transparent cell measured after shaking the tubular transparent cell containing the coated nickel hydroxide powder for a predetermined time and then taking the contents out of the tubular transparent cell Transmittance $B_0$: Transmittance of a tubular transparent cell measured after shaking the tubular transparent cell containing a nickel hydroxide powder for a predetermined time and then taking the contents out of the tubular transparent cell Transmittance $B_{max}$: Transmittance of a tubular transparent cell measured after shaking the tubular transparent cell, for a predetermined time, containing the nickel hydroxide powder and a cobalt compound powder containing cobalt in an amount corresponding to the amount of cobalt contained in the coating of the coated nickel hydroxide powder and then taking the contents out of the tubular transparent cell.

The adhesion properties of a coating made of cobalt hydroxide or cobalt oxyhydroxide of a coated nickel hydroxide powder is conventionally evaluated by a method in which a coated nickel hydroxide powder is mixed with a solvent such as water in a closed container, the container is shaken for a certain time, and the amount of a cobalt hydroxide coating peeled off is measured and evaluated based on the total amount of the coating. However, such a method has a problem that it is difficult to exactly separate the coating peeled off from the coating remaining on the coated nickel hydroxide powder to determine the amount of the coating peeled off; therefore, the error of a measured value is large. Further, after the coated nickel hydroxide powder is mixed with the solvent in the closed container and then shaken, the mixture is allowed to stand to separate the coating peeled off as a supernatant. However, the thus collected measurement sample needs to be dried; therefore, it takes a long time to obtain a measured value.

On the other hand, according to the evaluation method of the present invention, a measurement sample, such as a coated nickel hydroxide powder, necessary for measurement of each of the transmittances defined above is charged into a tubular transparent cell and shaken for a predetermined time, and then the powdery contents charged as a measurement sample are taken out of the tubular transparent cell. A coating peeled off adheres to the inner wall of the tubular transparent cell and remains in the tubular transparent cell. Therefore, coating adhesion properties can be evaluated simply by measuring the transmittance of the tubular transparent cell out of which the contents have been taken. That is, it is not necessary to forcedly separate the coating peeled off from the coating remaining on the coated nickel hydroxide powder; therefore, the error of a measured value can be made small, and coating adhesion properties can be evaluated without preparing a paste or an electrode plate. Further, the whole process of measuring the transmittance is performed by a dry method; therefore, a measurement time can be significantly reduced.

The evaluation method for the adhesion properties of a cobalt compound coating according to the present invention will be specifically described. First, a coated nickel hydroxide powder is charged into a tubular transparent cell, and the tubular transparent cell is tightly closed. The tubular transparent cell is shaken for a predetermined time, and then the coated nickel hydroxide powder contained in the tubular transparent cell is taken out to measure the transmittance A of the tubular transparent cell. The coated nickel hydroxide powder is brought into contact with the inner wall of the tubular transparent cell by the shaking; therefore, peeling stress is applied to a coating on the surface of nickel hydroxide particles. As a result, when having low adhesion properties, the coating is peeled off from the surface of particles of the nickel hydroxide powder and adheres to the inner wall of the cell so that the transmittance of the tubular transparent cell is reduced. On the other hand, when the coating has high adhesion properties, peeling-off of the coating is inhibited; therefore, the amount of the coating adhering to the inner wall of the cell is small so that the transmittance of the tubular transparent cell is high. Thus, the coating adhesion properties of the coated nickel hydroxide powder can be evaluated by measuring the transmittance of the tubular transparent cell after the shaking.

The coating adhesion properties of the coated nickel hydroxide powder can be qualitatively evaluated by measuring the transmittance A, but it is difficult to quantitatively determine whether or not the coating adhesion properties of the coated nickel hydroxide powder is excellent simply by measuring the transmittance A. For this reason, in the present invention, in addition to the measurement of the transmittance A using the coated nickel hydroxide powder, a transmittance B and a transmittance $B_{max}$ are also measured. The transmittance $B_0$ is measured using a nickel hydroxide powder that is a core material not coated with a cobalt compound, and the transmittance $B_{max}$ is measured using a mixture of the nickel hydroxide powder as a core material and a cobalt compound powder containing cobalt in an amount corresponding to the amount of cobalt contained in a coating formed when the nickel hydroxide powder is coated like the above-described coated nickel hydroxide powder.

Then, a transmittance ratio (%) is calculated from the measured transmittances A, $B_0$, and $B_{max}$ by a calculating formula $(A-B_{max})/(B_0-B_{max}) \times 100$ to obtain an index based on which a determination can be made as to whether or not the coating adhesion properties of the coated nickel hydroxide powder is excellent. It is considered that the transmittance A measured in such a manner as described above is equal to the transmittance $B_0$ when the coating is not peeled off at all, and is equal to the transmittance $B_{max}$ when the coating is all peeled off. Therefore, the transmittance ratio is in the range of 0 to 100%, and is higher when the adhesion properties of the coating to the nickel hydroxide particles as a core material is higher, which makes it possible to quantitatively evaluate the adhesion properties of the coating.

In the evaluation method, evaluation is made based on the transmittance ratio of $A-B_{max}$ to $B_0-B_{max}$; therefore, a stable result can be obtained which less varies depending on measurement conditions. The measurement conditions will be described below in detail with reference to a specific case where the transmittances are measured using a spectrocolorimeter.

A device for use in measuring the transmittances is not particularly limited as long as the transmittance of the tubular transparent cell can be measured, but a commonly-used absorptiometer or spectrocolorimeter is preferred due to its ease in measurement. The transmittances may be measured under usual measurement conditions. A measured value obtained by an absorptiometer is not a transmittance but an absorbance, but an absorbance can be converted to a transmittance by a calculation formula $H=-\log_{10}T$ (wherein H is an absorbance and T is a transmittance). Therefore, the transmittance ratio can be determined by converting absorbances obtained by an absorptiometer to transmittances.

Further, the cobalt compound powder charged into the tubular transparent cell to measure the transmittance $B_{max}$ is preferably a powder of cobalt hydroxide or cobalt oxyhydroxide that is a main ingredient of the coating of the coated nickel hydroxide powder, and is more preferably a powder having the same composition as the coating to be measured. The use of such a cobalt compound powder makes it possible to allow the cobalt compound powder to adhere to the inner wall of the cell in a situation close to that in which the coating peeled off from the coated nickel hydroxide powder adheres to the inner wall of the cell. This makes it possible to improve measurement accuracy.

Further, the cobalt compound powder used to measure the transmittance $B_{max}$ preferably has an average particle size of 0.3 to 5 μm. From the viewpoint of measurement accuracy, the cobalt compound powder preferably has a particle size nearly equal to that of the cobalt compound forming the coating of the coated nickel hydroxide powder. However, sufficient measurement accuracy can be achieved even when the cobalt compound powder used has such an average particle size because its particles are broken during shaking. If the average particle size of the cobalt compound powder is less than 0.3 μm, the cobalt compound powder is difficult to handle. If the average particle size of the cobalt compound powder exceeds 5 μm, there is a case where particles of the powder are not broken into smaller particles even by shaking so that measurement accuracy is undesirably reduced.

The reason why the tubular transparent cell is used to measure the transmittance is because a relatively large contact area between the coated nickel hydroxide powder and the inner wall of the transparent cell can be achieved and a long contact time between them during shaking can be achieved. The tubular transparent cell used may have any shape as long as the tubular transparent cell can be tightly closed and the tubular transparent cells used to measure all the transmittances have the same shape. However, the tubular transparent cell is preferably a circular or rectangular cylindrical transparent cell from the viewpoint of availability. Further, the tubular transparent cell used is made of, for example, styrene, hard glass, or quartz, but is preferably made of a transparent material that is not easily scratched by contact with particles of the coated nickel hydroxide powder during shaking, particularly preferably hard glass or quartz. When the inner wall of the tubular transparent cell is scratched during shaking, the transmittance is reduced so that a measurement error may become large.

The tubular transparent cell may have any capacity as long as a sample powder contained in the tubular transparent cell can be shaken and the tubular transparent cell can be used for measurement by a measurement device. In the case of a rectangular cylindrical cell, a standard cell having an optical path length of 10 mm may be used. In the case of a circular cylindrical cell, a cell having a diameter of 10 mm may be used. Further, the amount of the powder, such as the coated nickel hydroxide powder, charged into the tubular transparent cell may be arbitrarily selected depending on measurement conditions, but the ratio of the volume of the powder to the capacity of the cell is preferably about 30 to 55%. For example. When the amount of the coated nickel hydroxide powder is too small, there is a case where the amount of the coating that is peeled off and adheres to the inner wall of the cell is small so that measurement accuracy is reduced. On the other hand, if the amount of the coated nickel hydroxide powder is too large, there is a case where the coated nickel hydroxide powder in the cell cannot be sufficiently shaken so that the amount of the coating peeled off is smaller than reality. Also in this case, measurement accuracy is reduced. Further, when all the above-described three types of transmittances are measured, the amounts of the powders charged into the cells shall be the same to reduce errors caused by differences in the amounts of the powders.

In the evaluation method for coating adhesion properties according to the present invention, the tubular transparent cell containing a sample needs to be shaken for a predetermined time to bring the sample into frictional contact with the inner wall of the transparent cell to measure the transmittance of the transparent cell. At this time, as shown by an arrow a in FIG. 1, the shaking is preferably performed by performing at least reciprocating movement in a direction parallel to the central axis of a tubular transparent cell 1. Such a reciprocating movement performed in a direction parallel to the central axis makes it possible to maximize the time of contact, in other words, the distance of contact between the sample and the inner wall of the cell. This makes it possible to efficiently bring the sample into frictional contact with the inner wall of the cell.

Figure 2:
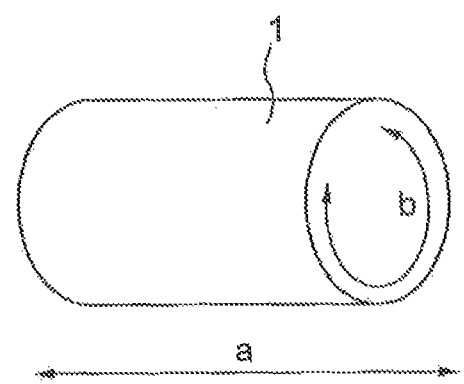
FIG. 2 A schematic diagram showing shaking by reciprocating movement in a direction parallel to the central axis of a tubular transparent cell simultaneously with rotational or semi-rotational movement around the central axis.

However, when the shaking is performed by performing only the reciprocating movement in a direction parallel to the central axis of the transparent cell, contact between the sample and the inner wall of the cell may occur only on a partial surface of the inner wall of the cell depending on the position or direction of the transparent cell set in a measurement device so that there is a fear that the measured value of the transmittance is biased and measurement accuracy is reduced. Therefore, in order to bring the sample into contact with the entire surface of the inner wall of the tubular transparent cell, the shaking is particularly preferably performed by performing the reciprocating movement in a direction parallel to the central axis shown by the arrow a simultaneously with rotational or semi-rotational movement around the central axis as shown by an arrow b in FIG. 2. This is because performing the reciprocating movement simultaneously with the rotational or semi-rotational movement makes it possible to allow the coating peeled off to uniformly adhere to the entire surface of the inner wall of the cell to reduce the error of the transmittance caused depending on the conditions of the cell set in a measurement device.

The shaking shall be performed under the same conditions all the time when all of the types of transmittances are measured. For example, the amplitude of the reciprocating movement is preferably set so as to achieve sufficient frictional contact, more specifically 50 to 250 mm. Further, the rate of the reciprocating movement is preferably in the range of 25 to 250 cm/sec. Further, the rate of the rotational or semi-rotational movement is preferably in the range of 180 to 360°/sec.

Further, in order to bring the sample into contact with the entire surface of the inner wall of the cell, the shaking is preferably performed by performing reciprocating movement in a direction parallel to the central axis of the cell, rotational movement around the central axis, and oscillation around the central point of the cell in combination at a reciprocating stroke of 50 to 250 mm and a frequency of 30 to 60 times/min. More specifically, the shaking may be performed by, for example, a TURBULA shaker mixer (container capacity: 2 L, e.g., TURBULA Type T2C manufactured by Willy A. Bachofen (WAB)). A device used for the shaking of the cell is not limited to the device exemplified above, and may be any device capable of shaking the cell in the same manner.

The time of the shaking is a certain time determined by, for example, a preliminary test so that a measurable transmittance can be stably obtained. If the shaking time is too short, the peeling-off of the coating is not completed or the coating peeled off does not sufficiently adhere to the inner wall of the cell; therefore, the adhesion properties of the coating cannot be properly evaluated. On the other hand, if the shaking time is longer than necessary, there is a case where breakage of the nickel hydroxide particles as a core material as well as peeling-off of the coating occurs, and the broken pieces of the particles adhere to the inner wall of the cell together with the coating peeled off; therefore, the coating adhesion properties of the coated nickel hydroxide powder cannot be properly evaluated.

Figure 3:
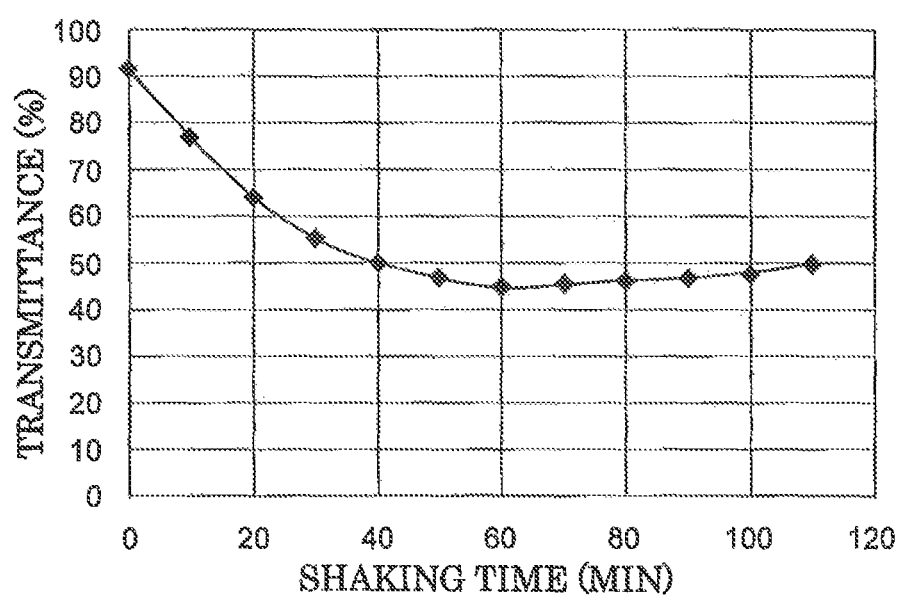
FIG. 3 A graph showing the relationship between shaking time and transmittance.

In order to avoid such a situation and properly evaluate the coating adhesion properties of the coated nickel hydroxide powder, the shaking time is preferably a total time of shaking performed until a reduction rate of the transmittance A per minute (%/min) previously experimentally determined by measuring the transmittance A every ten-minute shaking becomes 0.3% or less of an initial transmittance. More specifically, the transmittance A is measured every ten-minute shaking, the reduction rate of the transmittance A per minute (%/min) during each ten-minute shaking is determined, the time point when the reduction rate during ten-minute shaking becomes 0.3% or less of an initial transmittance (transmittance at the start of each ten-minute shaking) is regarded as the end point of shaking, and the total time of shaking until the end point is defined as a shaking time. If the shaking is finished at the time point when the reduction rate exceeds 0.3% of an initial transmittance, there is a case where a measured value of the transmittance widely varies so that an accurate transmittance ratio cannot be obtained. An example of a change of the transmittance with respect to the shaking time, experimentally determined by the present inventors, is shown in FIG. 3. It is to be noted that in this case, the shaking time is 60 minutes.

Hereinbelow, a coated nickel hydroxide powder for a positive electrode active material of alkaline secondary battery according to the present invention will be described. The coated nickel hydroxide powder according to the present invention is a coated nickel hydroxide powder for a positive electrode active material of alkaline secondary battery, comprising nickel hydroxide particles having a coating made of a cobalt compound on a surface thereof, wherein when a transmittance A, a transmittance $B_0$, and a transmittance $B_{max}$ are defined as above, a transmittance ratio (%) represented by $(A-B_{max})/(B_0-B_{max})\times 100$ is 30% or higher, preferably 50% or higher.

The definitions of the transmittances are described again below for confirmation.

Transmittance A: Transmittance of a tubular transparent cell measured after shaking the tubular transparent cell containing the coated nickel hydroxide powder for a predetermined time and then taking the contents out of the tubular transparent cell Transmittance $B_0$: Transmittance of a tubular transparent cell measured after shaking the tubular transparent cell containing a nickel hydroxide powder for a predetermined time and then taking the contents out of the tubular transparent cell Transmittance $B_{max}$: Transmittance of a tubular transparent cell measured after shaking the tubular transparent cell, for a predetermined time, containing the nickel hydroxide powder and a cobalt compound powder containing cobalt in an amount corresponding to an amount of cobalt contained in the coating of the coated nickel hydroxide powder and then taking the contents out of the tubular transparent cell The transmittance ratio (%) represented by $(A-B_{max})/(B_0-B_{max})\times 100$ can be determined by the above evaluation method for coating adhesion properties according to the present invention. When the transmittance ratio is 30% or higher, peeling-off of the cobalt compound coating is significantly inhibited; therefore, the coated nickel hydroxide powder is suitable for positive electrode active material of alkaline secondary battery. It is to be noted that the transmittance ratio does not exceed 100% by definition, and in the present invention, the upper limit of the transmittance ratio is practically about 90%.

On the other hand, if the transmittance ratio is less than 30%, the adhesion properties of the coating on the surface of the nickel hydroxide particles is poor; therefore, the cobalt compound coating is easily peeled off. When a coated nickel hydroxide powder poor in coating adhesion properties is used, the amount of its coating peeled off during preparation of a paste or an electrode plate in the process of battery production is large. As a result, an alkaline secondary battery produced using such a coated nickel hydroxide powder poor in coating adhesion properties is poor in battery characteristics, especially positive electrode utilization ratio during high-load electrical charge or output characteristics.

The nickel hydroxide particles used as a core material to be coated with the cobalt compound preferably has a composition represented by the following general formula: $Ni_{1-x-y}Co_xM_y(OH)_2$ (wherein x is 0.005 to 0.05, y is 0.005 to 0.05, M is at least one element selected from Ca, Mg, and Zn).

If x that represents a cobalt content in the above general formula is less than 0.005, the effect of improving charge efficiency achieved by adding cobalt cannot be obtained. On the other hand, if x exceeds 0.05, battery performance is degraded due to a reduction in discharge voltage. If y that represents the amount of M contained as an additive element in the above formula is less than 0.005, the effect of reducing a change in the volume of nickel hydroxide during discharge and charge achieved by adding the element M cannot be obtained. On the other hand, if y exceeds 0.05, the effect of reducing a change in the volume of nickel hydroxide can be obtained, but beyond that, a reduction in battery capacity is caused so that battery performance is undesirably degraded.

Further, the amount of cobalt contained in the cobalt compound coating of the coated nickel hydroxide powder is preferably 1 to 10 mass %, more preferably 3 to 7 mass % with respect to the total mass of the coated nickel hydroxide powder. If the amount of cobalt contained in the coating is less than 1 mass %, there is a case where the effect of coating the surface of the cobalt hydroxide particles is not sufficiently obtained due to the shortage of the amount of the cobalt compound constituting the coating. On the other hand, if the amount of cobalt contained in the coating exceeds 10 mass %, the amount of the cobalt compound constituting the coating increases, but the coating effect is not further improved. It is to be noted that the nickel hydroxide particles used as a core material are preferably uniformly coated with the cobalt compound. The nickel hydroxide particles may be coated with small islands shape of the cobalt compound as long as they are uniformly coated, but are more preferably coated with a layer of the cobalt compound, and even more preferably fully coated with the cobalt compound.

Further, the cobalt compound constituting the coating contains, as a main ingredient, cobalt oxyhydroxide or a mixture of cobalt oxyhydroxide and cobalt hydroxide. The amount of cobalt contained in the coating is preferably 90 mass % or more, more preferably 95 mass % or more with respect to the total mass of metal elements contained in the coating. It is to be noted that an additive element, such as Ca, Mg, or Zn, can be added to the coating to improve the battery characteristics of a battery having a positive electrode using the coated nickel hydroxide powder. However, if the amount of cobalt contained in the coating is less than 90 mass %, there is a case where conductivity cannot be sufficiently improved by the coating.

The coated nickel hydroxide powder is obtained by coating nickel hydroxide particles as a core material with a cobalt compound by a wet method. For example, the coated nickel hydroxide powder can be produced in the following manner: a nickel hydroxide powder is dispersed in water to prepare a suspension, and then an aqueous cobalt salt solution and an aqueous alkali solution are supplied to the stirred suspension so that nickel hydroxide particles are coated with a cobalt compound crystallized thereon by neutralization. Hereinbelow, a method for producing the coated nickel hydroxide powder will be specifically described.

A nickel hydroxide powder is dispersed in water to prepare a suspension, and then an aqueous cobalt salt solution and an aqueous alkali solution are supplied to the stirred suspension. At this time, the pH of the suspension mixed with the aqueous cobalt salt solution and the aqueous alkali solution is kept at 8 or higher as measured at 25° C. Further, the ratio of the supply rate $\rho$ (mol/sec) of the aqueous cobalt salt solution to the product of the supply width d (cm) of the aqueous cobalt salt solution in a direction orthogonal to the flow direction of the suspension and the flow velocity v (cm/sec) of the suspension in a contact portion between the surface of the suspension and the aqueous cobalt salt solution supplied thereto, that is, $\rho/(d \times v)$ is controlled to be $3.5 \times 10^{-4}$ mol/cm² or less. This makes it possible to obtain a coated nickel hydroxide powder whose particle surface is coated with a cobalt compound.

As described above, when an aqueous cobalt salt solution and an aqueous alkali solution are added to a stirred suspension, in which a nickel hydroxide powder is dispersed in water, so that the surface of the nickel hydroxide powder is coated with cobalt hydroxide by a crystallization reaction caused by neutralization, cobalt is present in its ionic state in a region of the suspension where a pH value is low, but deposition of cobalt hydroxide gradually starts as the pH value increases. At this time, when nickel hydroxide particles are present near cobalt hydroxide, the cobalt hydroxide is deposited on the surface of the nickel hydroxide particles that are energetically more stable.

When the concentration of cobalt ions rapidly increases and exceeds its critical supersaturation in the pH range of the suspension in which cobalt ions are present, cobalt hydroxide is deposited alone in water even when nickel hydroxide particles are not present near the cobalt hydroxide. However, when the pH value of the suspension is low, more specifically when the pH is less than 8, the deposition rate of cobalt hydroxide is low; therefore, cobalt hydroxide is not deposited alone even when the concentration of cobalt ions exceeds it critical supersaturation.

On the other hand, when the pH value of the suspension in which cobalt ions are present is 8 or higher, the critical supersaturation of the concentration of cobalt ions is reduced Therefore, the concentration of cobalt ions easily exceeds its critical supersaturation when it increases. As a result, cobalt hydroxide is deposited alone without adhering to the surface of nickel hydroxide particles. Such cobalt hydroxide deposited alone adheres to the surface of nickel hydroxide particles when a nickel hydroxide slurry is filtered. In this case, however, the cobalt hydroxide sparsely adheres to the surface of nickel hydroxide particles and is therefore poor in uniformity, and in addition, the cobalt hydroxide is very poor in adhesion properties because adhesion between the cobalt hydroxide and the nickel hydroxide particles is achieved simply by filtration.

Therefore, in order to uniformly form cobalt hydroxide having high adhesion properties on the surface of nickel hydroxide particles, the pH (as measured at 25° C.) of a suspension of nickel hydroxide particles is controlled to be in the range of 8 or higher, and the concentration of cobalt ions in the suspension in such a pH range is kept at or below a concentration at which cobalt hydroxide is not deposited alone. According to such a method, cobalt hydroxide is deposited on the surface of nickel hydroxide particles in accordance with the surface structure of nickel hydroxide; therefore, a coating having extremely high adhesion properties is uniformly formed on the surface of the particles.

In order to reliably deposit such cobalt hydroxide excellent in uniformity and adhesion properties, it is important to avoid the creation of a region where the concentration of cobalt ions is high. This is achieved by reducing the ratio of the supply rate of the aqueous cobalt salt solution to the amount of the suspension flowing into a portion where the aqueous cobalt salt solution is supplied to and mixed with the suspension. That is, it is necessary to prevent the appearance of a region where the concentration of cobalt ions is extremely high in the suspension. This is achieved by reducing the supply rate of the aqueous cobalt salt solution to sufficiently reduce the concentration of a cobalt salt even when the amount of the suspension mixed with the aqueous cobalt salt solution is small, or by increasing the amount of the suspension mixed with the aqueous cobalt salt solution to diffuse the aqueous cobalt salt solution supplied to the suspension as quickly as possible for dilution.

The amount of the suspension mixed with the aqueous cobalt salt solution may be considered as the amount of the suspension flowing into a portion where the aqueous cobalt salt solution supplied comes into contact with the surface of the suspension and is mixed with the suspension. The mixing is initially performed in an extremely short period of time; therefore, when the flow velocity of the suspension is sufficiently high, the amount of suspension mixed with the aqueous cobalt salt solution can be considered as the surface of the suspension that comes into contact with the aqueous cobalt salt solution per unit time. That is, the amount of the suspension mixed with the aqueous cobalt salt solution can be considered as the product of the supply width (d) of the aqueous cobalt salt solution in a direction orthogonal to the flow direction of the suspension and the surface flow velocity (v) of the suspension in a contact portion between the surface of the suspension and the aqueous cobalt salt solution. It is to be noted that when the contact portion between the surface of the suspension and the aqueous cobalt salt solution is circular, the supply width (d) of the aqueous cobalt salt solution in a direction orthogonal to the flow direction of the suspension is equal to the diameter of the circular contact portion. Further, when it is difficult to actually measure the surface flow velocity of the suspension, the surface flow velocity of the suspension can be easily determined by simulation.

In the present invention, the ratio of the supply rate ($\rho$) of the aqueous cobalt salt solution to the product of the supply width (d) of the aqueous cobalt salt solution in a direction orthogonal to the flow direction of the suspension and the flow velocity (v) of the suspension in a contact portion between the surface of the suspension and the aqueous cobalt salt solution, that is, $\rho/(d \times v)$ needs to be small. More specifically, the ratio $\rho/(d \times v)$ needs to be $3.5 \times 10^{-4}$ mol/cm$^2$ or less, and is preferably $2.0 \times 10^{-4}$ mol/cm$^2$ or less. If the ratio $\rho/(d \times v)$ exceeds $3.5 \times 10^{-4}$ mol/cm$^2$, a region where high concentration of cobalt ions appears so that cobalt hydroxide is deposited alone. It is to be noted that the lower limit of the ratio $\rho/(d \times v)$ is not particularly limited, but is preferably $0.01 \times 10^{-4}$ mol/cm$^2$ or more because a reduction in the supply rate ($\rho$) reduces productivity.

Here, when the opening size of a supply port for the aqueous cobalt salt solution is small enough to supply the aqueous cobalt salt solution as a stable liquid flow whose cross-section is substantially the same in size as the opening of the supply port, the area of the contact portion, that is, the area of a portion where the aqueous cobalt salt solution supplied from the supply port toward the surface of the suspension first comes into contact with the surface of the suspension coincides with the projected area of the supply port onto the surface of the suspension. That is, when the opening size of the supply port for the aqueous cobalt salt solution is small as described above, the area of the contact portion between the surface of the suspension and the aqueous cobalt salt solution may be regarded as the projected area of the supply port onto the surface of the suspension. On the other hand, when the opening size of the supply port for the aqueous cobalt salt solution is larger than that described above, the flow velocity of the aqueous cobalt salt solution discharged from the supply port is generally low, which makes it impossible to uniformly supply the aqueous cobalt salt solution from the supply port and makes it difficult to control the area of the contact portion between the surface of the suspension and the aqueous cobalt salt solution.

Therefore, in order to supply the aqueous cobalt salt solution as a stable liquid flow from the supply port, the area of opening of the supply port is preferably 0.01 to 1.0 cm$^2$. If the area of opening of the supply port is less than 0.01 cm$^2$, there is a case where the supply rate of the aqueous cobalt salt solution is low; therefore, sufficient productivity cannot be achieved. On the other hand, if the cross-sectional area of the supply port exceeds 1.0 cm$^2$, there is a case where the aqueous cobalt salt solution is not sufficiently diffused because it is difficult to uniformly supply the aqueous cobalt salt solution from the supply port; therefore, the amount of the aqueous cobalt salt solution supplied varies even when the contact portion between the surface of the suspension and the aqueous cobalt salt solution is within a region defined by the projected area of the supply port onto the surface of the suspension so that the aqueous cobalt salt solution is likely to be intensively supplied to a particular portion.

It is to be noted that when the aqueous cobalt salt solution is supplied by spraying it from the supply port onto the surface of the suspension with a spray nozzle or the like, the area of contact between the aqueous cobalt salt solution and the surface of the suspension can be regarded as the area of a region where the aqueous cobalt salt solution is sprayed onto the surface of the suspension. Alternatively, two or more supply ports may be provided to increase the total amount of the aqueous cobalt salt solution supplied to increase productivity as long as, as described above, the aqueous cobalt salt solution can be uniformly supplied from the supply ports to the surface of the suspension. The number of supply ports is not particularly limited, and may be determined in consideration of the supply rate of the aqueous cobalt salt solution supplied from each of the supply port or the product of the supply width of the aqueous cobalt salt solution and the flow velocity of the suspension.

Further, also when the pH value of the suspension rapidly increases in a portion where the aqueous cobalt salt solution is supplied, the concentration at which cobalt hydroxide is not deposited alone in such a high pH range, that is, critical saturation concentration is reduced so that cobalt hydroxide is easily deposited alone As a result, cobalt hydroxide is started to be deposited alone even when nickel hydroxide particles are not present near the cobalt hydroxide; therefore, cobalt hydroxide poor in adhesion properties and uniformity is likely to adhere to the surface of nickel hydroxide particles. In order to prevent this, it is preferred that the aqueous alkali solution supplied simultaneously with the aqueous cobalt salt solution is also diffused at a sufficiently high speed to inhibit the creation of a high pH region due to a rapid increase in the concentration of the aqueous alkali solution.

For example, if the supply rate of a cobalt salt to the surface of the suspension per unit area exceeds 0.01 mol/cm$^2$·min even when the flow velocity of the suspension is sufficiently high, a reaction occurs due to contact between a high pH region and the aqueous cobalt salt solution before the aqueous alkali solution is sufficiently diffused in the suspension when the distance between the supply position of the aqueous cobalt salt solution added and the supply position of the aqueous alkali solution added is short. In this case, there is a high possibility that cobalt hydroxide poor in adhesion properties and uniformity is deposited.

In order to avoid this, the ratio of the distance (D) (cm) of separation between the supply position of the aqueous cobalt salt solution and the supply position of the aqueous alkali solution to the above-described ratio of the supply rate $\rho$ of the aqueous cobalt salt solution to the product of the supply width d of the aqueous cobalt salt solution and the flow velocity v of the suspension $\{\rho/(d \times v)\}$, that is, $D/\{\rho/(d \times v)\}$ is preferably $0.5 \times 10^5$ cm$^3$/mol or more, more preferably $1.0 \times 10^5$ cm$^3$/mol or more. It is to be noted that the upper limit of the ratio $D/\{\rho/(d \times v)\}$ is limited by the supply rate ($\rho$) or the size of a reactor, and is therefore usually about $100 \times 10^5$ cm$^3$/mol.

Hereinbelow, the method for producing a cobalt-hydroxide-coated nickel hydroxide powder according to the present invention will be more specifically described. It is to be noted that the production method according to the present invention can achieve improvement in productivity when performed in a continuous manner, but is preferably performed in a batch manner to form a uniform coating on nickel hydroxide particles. Therefore, the production method according to the present invention will be described below with reference to a case where a cobalt-hydroxide-coated nickel hydroxide powder is produced in a batch manner.

First, a suspension of a nickel hydroxide powder, an aqueous solution of a cobalt salt, and an aqueous solution of an alkali are prepared. The nickel hydroxide powder used as a core material preferably has an average particle size of 6 to 12 μm so that a battery using a resulting coated-nickel hydroxide powder as a positive electrode material can achieve excellent battery characteristics. Further, the concentration of the nickel hydroxide powder in the suspension is preferably 400 to 1200 g/l. If the concentration of the nickel hydroxide powder is less than 400 g/l, there is a case where cobalt hydroxide is deposited alone in the suspension due to the lack of surface active sites of nickel hydroxide particles where deposition of cobalt hydroxide occurs. On the other hand, the concentration of the nickel hydroxide powder exceeds 1200 g/l, there is a case where the suspension cannot be sufficiently stirred due to an increase in viscosity so that a cobalt hydroxide coating is non-uniformly formed.

The cobalt salt is not particularly limited as long as the cobalt salt is a water-soluble cobalt compound from which cobalt hydroxide is generated by pH control. More specifically, the cobalt salt is preferably cobalt sulfate or cobalt chloride, more preferably cobalt sulfate not contaminated with halogens. The alkali is not particularly limited, but is preferably water-soluble sodium hydroxide or potassium hydroxide, and is particularly preferably sodium hydroxide from the viewpoint of costs.

The suspension of the nickel hydroxide powder is preferably prepared by dispersing nickel hydroxide particles in pure water or the like to prevent impurity incorporation. The aqueous cobalt salt solution or the aqueous alkali solution is also preferably prepared by dissolving a cobalt salt or an alkali in pure water, respectively. It is to be noted that the concentrations of the aqueous cobalt salt solution and the aqueous alkali solution are not particularly limited as long as redeposition does not occur in tubes or the like of an apparatus used and a problem does not occur even when the concentration of nickel hydroxide in the suspension varies, and an aqueous cobalt salt solution and an aqueous alkali solution having predetermined concentrations that depend on, for example, the concentration of the suspension can be used.

When the production method is performed in a batch manner, the aqueous cobalt salt solution and the aqueous alkali solution for forming a coating are continuously supplied to a reactor containing the stirred suspension of the nickel hydroxide powder used as a core material. As a result, the surface of nickel hydroxide particles is coated with cobalt hydroxide crystallized out by neutralization so that a cobalt-hydroxide-coated nickel hydroxide powder is produced. The reactor used in the batch-type production method is not particularly limited, but preferably has a stirring device and a liquid temperature-regulating system to form a uniform coating on the surface of particles of the nickel hydroxide powder.

The aqueous cobalt salt solution and the aqueous alkali solution need to be supplied individually. The aqueous cobalt salt solution and the aqueous alkali solution may be supplied at the same time, or may be supplied together with a part of the suspension to the residual suspension contained in the reactor. However, when all these liquids are previously mixed and supplied as a mixed liquid to the reactor, there is a case where a reaction occurs in the mixed liquid so that cobalt hydroxide is deposited alone. Further, when the aqueous cobalt salt solution and the aqueous alkali solution are not supplied to the suspension individually, there is a case where the amount of a cobalt hydroxide coating formed on the surface of nickel hydroxide particles is not uniform among the particles.

The pH of the suspension at the time when the aqueous cobalt salt solution and the aqueous alkali solution supplied are mixed until an equilibrium state is achieved is preferably kept in the range of 8 to 11.5 as measured at 25° C., and is more preferably kept in the range of 9.5 to 10.5 as measured at 25° C. If the pH value of the suspension is less than 8, the deposition rate of cobalt hydroxide is too low; therefore, productivity is reduced. On the other hand, if the pH value of the suspension exceeds 11.5, there is a case where generated cobalt hydroxide is likely to gelate; therefore, it is difficult to form an excellent coating.

Further, the pH of the suspension is preferably kept at a certain value in the range of 8 to 11.5 as measured at 25° C. and controlled so that its fluctuation range is within ±0.2. If the fluctuation range of the pH exceeds the above limit, there is a fear that the amount of a cobalt hydroxide coating varies. It is preferred that the pH of the suspension is continuously measured with, for example, a pH controller using a glass electrode method, and the flow rate of the aqueous alkali solution is continuously feedback-controlled with the pH controller so that the pH is kept constant within the above fluctuation range.

The temperature of the suspension is preferably in the range of 30 to 60° C. before and after the aqueous cobalt salt solution and the aqueous alkali solution are added. If the temperature of the suspension is less than 30° C., cobalt hydroxide is slowly deposited due to a low reaction rate. On the other hand, if the temperature of the suspension exceeds 60° C., cobalt hydroxide is likely to be non-uniformly deposited on the surface of nickel hydroxide particles due to too high a reaction rate. Further, the temperature of the suspension is preferably kept at a certain value within the above temperature range and controlled so that its fluctuation range is within ±1° C. If the fluctuation range of the temperature of the suspension exceeds the above limit, there is a fear that the concentration of impurities in deposited cobalt hydroxide varies so that a battery using a resulting coated nickel hydroxide powder does not have stable characteristics.

According to the above production method of the present invention, it is possible to obtain a nickel hydroxide powder whose particles have a uniform cobalt hydroxide coating tightly adhering to the surface thereof. Further, after the surface of the nickel hydroxide particles is coated with cobalt hydroxide in the suspension in such a manner as described above, cobalt hydroxide that coats the surface of the nickel hydroxide particles may be oxidized to cobalt oxyhydroxide by, for example, supplying air or oxygen or adding an oxidizer to the stirred suspension. Particularly, when the oxidation is performed with air or oxygen, the pH of the suspension is preferably kept at 12.5 to 13.5 as measured at 25° C. to efficiently achieve oxidation even by air or oxygen.

EXAMPLES

Example 1

Six kilograms of a spherical nickel hydroxide powder having an average particle size of 8 μm was placed in a reactor having a diameter of 25 cm and a depth of 30 cm, and water was added to the reactor so that a total volume was 10 liters. Then, the nickel hydroxide powder was dispersed in the water by stirring using a propeller stirrer at a rotation speed of 500 rpm to prepare a suspension of the nickel hydroxide powder.

The suspension was kept stirred, and when the surface flow velocity of the suspension at a portion where a 1.6 mol/l aqueous cobalt sulfate solution was to be added as an aqueous cobalt salt solution reached a steady state of 15.8 cm/sec, 2.017 liters of the aqueous cobalt sulfate solution was added in 2 hours at a supply rate of 16.8 ml/sec using a roller pump from one supply port having a diameter of 2 mm. At the same time, a 24 mass % aqueous sodium hydroxide solution was added from one supply port to a portion where the surface flow rate of the suspension was the same as described above under control using a roller pump interfacing with a pH controller so that the pH of the suspension was in the range of 10.2±0.2 as measured at 25° C. The supply port for the aqueous sodium hydroxide solution was provided 15 cm away from the supply port for the aqueous cobalt sulfate solution in a horizontal direction, and had the same diameter as the supply port for the aqueous cobalt sulfate solution.

At this time, the ratio of the supply rate $\rho$ (mol sec) of the aqueous cobalt salt solution to the product of the supply width d (cm) of the aqueous cobalt salt solution in a direction orthogonal to the flow direction of the suspension and the flow velocity v (cm/sec) of the suspension in a contact portion between the surface of the suspension and the aqueous cobalt salt solution supplied thereto, that is, $\rho/(d \times v)$ was $1.42 \times 10^{-4}$ mol/cm². The ratio of the distance D (cm) between the supply position of the aqueous cobalt salt solution and the supply position of the aqueous alkali solution to the ratio of the supply rate $\rho$ of the aqueous cobalt salt solution to the product of the supply width d of the aqueous cobalt salt solution and the flow velocity v of the suspension, that is, $D/\{\rho/(d \times v)\}$ was $1.06 \times 10^5$ cm³/mol. It is to be noted that the temperature of the suspension during reaction was controlled to be 50° C.

As a result of the above operation, cobalt hydroxide was deposited on the surface of particles of the nickel hydroxide powder in the suspension so that a cobalt-hydroxide-coated nickel hydroxide powder was obtained whose particles had a cobalt hydroxide coating on the surface thereof. After the total amounts of the aqueous cobalt sulfate solution and the aqueous sodium hydroxide solution were added in the above operation, air was blown into the stirred suspension for 4 hours while the pH of the suspension was kept at 12.8 as measured at 25° C. by further adding the aqueous sodium hydroxide solution to oxidize cobalt hydroxide deposited on the surface of the nickel hydroxide particles to cobalt oxyhydroxide.

Figure 4:
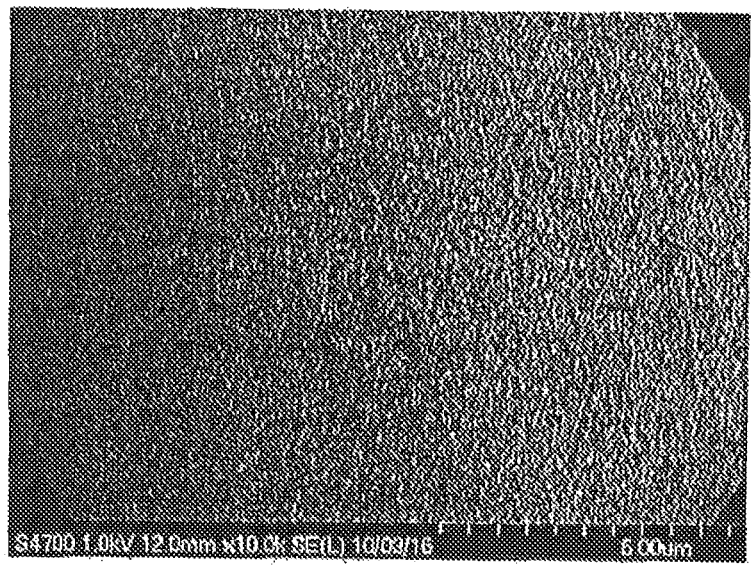
FIG. 4 A scanning electron micrograph of a cobalt oxyhydroxide-coated nickel hydroxide powder prepared in Example 1.

Then, the suspension was subjected to solid-liquid separation using a filter press to collect the powder, and the powder was washed with water and again subjected to filtration. Then, the obtained powder was dried in a vacuum drier at 120° C. for 20 hours to obtain 6.3 kg of a cobalt oxyhydroxide-coated nickel hydroxide powder. The obtained cobalt oxyhydroxide-coated nickel hydroxide powder was dark brown. The powder was observed with a SEM to evaluate the state of the cobalt oxyhydroxide coating. As a result, as shown in FIG. 4, the nickel hydroxide particles were found to have a uniform coating layer.

Then, 10.0 g of the cobalt oxyhydroxide-coated nickel hydroxide powder was placed in a circular cylindrical transparent cell made of quartz glass (inner diameter 1 cm×length 12 cm, internal capacity: 12 ml), and the circular cylindrical transparent cell was tightly closed. The ratio of the volume of the cobalt oxyhydroxide-coated nickel hydroxide powder to the capacity of the circular cylindrical transparent cell was 46%. The circular cylindrical transparent cell was shaken for 1 hour using a shaker mixer (TURBULA Type T2C manufactured by Willy A. Bachofen (WAB)). It is to be noted that the shaking was performed by performing reciprocating movement in a direction parallel to the central axis of the transparent cell (stroke: 220 cm, speed: 154 cm/sec), rotational movement around the central axis (speed: 250°/sec), and oscillation around the central point of the transparent cell at the same time.

After the completion of the shaking, the contents were taken out of the circular cylindrical transparent cell. The transmittance of the remaining circular cylindrical transparent cell was measured using a spectrocolorimeter (SE6000 manufactured by NIPPON DENSHOKU INDUSTRIES CO., LTD.) at a measuring wavelength of 380 to 780 nm. As a result, the transmittance A measured using the cobalt oxyhydroxide-coated nickel hydroxide powder was 45%.

On the other hand, a transmittance $B_0$ was measured in the same manner as described above except that a non-coated nickel hydroxide powder was used in the same volume as the cobalt oxyhydroxide-coated nickel hydroxide powder. As a result, the transmittance $B_0$ was 92%. Further, a transmittance B was measured in the same manner as described above except that a cobalt hydroxide powder (average particle size of primary particles measured with a SEM: 0.8 μm) prepared by the above method without adding a nickel hydroxide powder and a non-coated nickel hydroxide powder were mixed in a mass ratio between the coating and the core material. As a result, the transmittance $B_{max}$ was 23%.

The transmittance ratio (%) of the cobalt oxyhydroxide-coated nickel hydroxide powder was calculated from the transmittance A, the transmittance $B_0$, and the transmittance $B_{max}$ using the formula $(A-B_{max}) \times 100$. As a result, the transmittance ratio was $(45-23)/(92-23)=31.8\%$.

Example 2

A reactor having a diameter of 84 cm and a depth of 100 cm was prepared, 240 kg of the same nickel hydroxide powder as used in Example 1 was placed in the reactor, and water was added to the reactor so that a total volume was 350 liters. Then, the nickel hydroxide powder was dispersed in the water by stirring using a propeller stirrer at a rotation speed of 350 rpm to prepare a suspension of the nickel hydroxide powder.

Then, 80.7 liters of an aqueous cobalt sulfate solution adjusted to a concentration of 1.6 mol/l was added in 2 hours using a roller pump from 10 supply ports each having a diameter of 2 mm at an addition rate of 67.2 ml/min per supply port to positions where the surface flow velocity of the suspension was 49.7 cm/sec. At the same time, a 24 mass % aqueous sodium hydroxide solution was added to its supply position under control using a roller pump interfacing with a pH controller so that the pH of the suspension was in the range of 10.2±0.2 as measured at 25° C. The supply position of the aqueous sodium hydroxide solution was 20 cm away from the nearest one of contact portions between the aqueous cobalt sulfate solution supplied from the 10 supply ports and the surface of the suspension, and the surface flow velocity of the suspension in the supply position of the aqueous sodium hydroxide solution was the same as described above. In this way, cobalt hydroxide was deposited on the surface of nickel hydroxide particles.

At this time, the ratio of the supply rate ρ (mol/sec) of the aqueous cobalt salt solution to the product of the supply width d (cm) of the aqueous cobalt salt solution in a direction orthogonal to the flow direction of the suspension and the flow velocity v (cm/sec) of the suspension in each of the contact portions between the surface of the suspension and the aqueous cobalt salt solution supplied thereto, that is, ρ/(d×v) was $1.80 \times 10^{-4}$ mol/cm². With regard to the supply port for the aqueous cobalt salt solution nearest the supply position of sodium hydroxide, the ratio of the distance D (cm) between the supply position of the aqueous cobalt salt solution and the supply position of the aqueous alkali solution to the ratio of the supply rate ρ of the aqueous cobalt salt solution to the product of the supply width d of the aqueous cobalt salt solution and the flow velocity v of the suspension, that is, D/{ρ/(d×v)} was $1.11 \times 10^5$ cm³/mol. It is to be noted that the temperature of the suspension during reaction was controlled to be 50° C.

As a result of the above operation, cobalt hydroxide was deposited on the surface of particles of the nickel hydroxide powder so that a cobalt-hydroxide-coated nickel hydroxide powder was obtained whose particles had a cobalt hydroxide coating on the surface thereof. Further, cobalt hydroxide deposited on the surface of the nickel hydroxide particles was oxidized to cobalt oxyhydroxide in the same manner as in Example 1.

Then, the suspension was subjected to solid-liquid separation using a filter press to collect the powder, and the powder was washed with water and again subjected to filtration. Then, the obtained powder was dried in a vacuum drier at 120° C. for 20 hours to obtain 252 kg of a cobalt oxyhydroxide-coated nickel hydroxide powder. The obtained cobalt oxyhydroxide-coated nickel hydroxide powder was dark brown. The powder was observed with a SEM to evaluate the state of the cobalt oxyhydroxide coating. As a result, the nickel hydroxide particles were found to have a uniform coating layer.

Transmittances A, $B_0$, and $B_{max}$ were determined in the same manner as in Example 1, and the transmittance ratio (%) of the cobalt oxyhydroxide-coated nickel hydroxide powder was calculated using the formula $(A-B_{max})/(B_0-B_{max}) \times 100$. As a result, the transmittance ratio was 31.2%.

Example 3

A reactor having a diameter of 190 cm and a depth of 220 cm was prepared, 2880 kg of the same nickel hydroxide powder as used in Example 1 was placed in the reactor, and water was added to the reactor so that a total volume was 3000 liters. Then, the nickel hydroxide powder was dispersed in the water by stirring using a propeller stirrer at a rotation speed of 150 rpm to prepare a suspension of the nickel hydroxide powder.

Then, 968.3 liters of an aqueous cobalt sulfate solution adjusted to a concentration of 1.6 mol/l was added in 2 hours using a roller pump from 2 nozzles at an addition rate of 4035 ml/min per nozzle by spraying the aqueous cobalt sulfate solution in a circular pattern, having a diameter of 500 mm onto the surface of the suspension where the surface flow velocity of the suspension was 126.5 cm/sec. At the same time, a 24 mass % aqueous sodium hydroxide solution was added to its supply position under control using a roller pump interfacing with a pH controller so that the pH of the suspension was in the range of 10.2±0.2 as measured at 25° C., The supply position of the aqueous sodium hydroxide solution was 20 cm away from the nearest one of contact portions between the aqueous cobalt sulfate solution supplied from the two nozzles and the surface of the suspension, and the surface flow velocity of the suspension in the supply position of the aqueous sodium hydroxide solution was the same as described above. In this way, cobalt hydroxide was deposited on the surface of nickel hydroxide particles.

At this time, the ratio of the supply rate ρ (mol/sec) of the aqueous cobalt salt solution to the product of the supply width d (cm) of the aqueous cobalt salt solution in a direction orthogonal to the flow direction of the suspension and the flow velocity v (cm/sec) of the suspension in each of the contact portions between the surface of the suspension and the aqueous cobalt salt solution supplied thereto, that is, ρ/(d×v) was $1.70 \times 10^{-5}$ mol/cm². With regard to the nozzle for the aqueous cobalt salt solution nearest the supply position of sodium hydroxide, the ratio of the distance D (cm) between the supply position of the aqueous cobalt salt solution and the supply position of the aqueous alkali solution to the ratio of the supply rate ρ of the aqueous cobalt salt solution to the product of the supply width d of the aqueous cobalt salt solution and the flow velocity v of the suspension, that is, D/{ρ/(d×v)} was $11.8 \times 10^5$ cm³/mol. It is to be noted that the temperature of the suspension during reaction was controlled to be 50° C.

As a result of the above operation, cobalt hydroxide was deposited on the surface of particles of the nickel hydroxide powder so that a cobalt-hydroxide-coated nickel hydroxide powder was obtained whose particles had a cobalt hydroxide coating on the surface thereof. Further, cobalt hydroxide deposited on the surface of the nickel hydroxide particles was oxidized to cobalt oxyhydroxide in the same manner as in Example 1.

Then, the suspension was subjected to solid-liquid separation using a filter press to collect the powder, and the powder was washed with water and again subjected to filtration Then, the obtained powder was dried in a vacuum drier at 120° C. for 20 hours to obtain 252 kg of a cobalt oxyhydroxide-coated nickel hydroxide powder. The obtained cobalt oxyhydroxide-coated nickel hydroxide powder was dark brown. The powder was observed with a SEM to evaluate the state of the cobalt oxyhydroxide coating. As a result, the nickel hydroxide particles were found to have a uniform coating layer.

Transmittances A, $B_0$, and $B_{max}$ were determined in the same manner as in Example 1, and the transmittance ratio (%) of the cobalt oxyhydroxide-coated nickel hydroxide powder was calculated using the formula $(A-B_{max})/(B_0-B_{max}) \times 100$. As a result, the transmittance ratio was 33.5%.

Comparative Example 1

A cobalt-hydroxide-coated nickel hydroxide powder was obtained in the same manner as in Example 1 except that the rotation speed of the propeller stirrer was changed to 300 rpm and that an aqueous cobalt sulfate solution and an aqueous sodium hydroxide solution were added when the surface flow velocity of the suspension in a portion where the aqueous cobalt sulfate solution was to be added reached a steady state of 5 cm/sec. Further, cobalt hydroxide deposited on the surface of nickel hydroxide particles was oxidized in the same manner as in Example 1 to obtain a cobalt oxyhydroxide-coated nickel hydroxide powder.

At this time, the ratio of the supply rate ρ of the aqueous cobalt salt solution to the product of the supply width d of the aqueous cobalt salt solution supplied to the suspension and the flow velocity v of the suspension, that is, ρ/(d×v) was $4.48 \times 10^{-4}$ mol/cm². The ratio of the distance D between the supply position of the aqueous cobalt salt solution and the supply position of the aqueous alkali solution to the ratio of the supply rate ρ of the aqueous cobalt salt solution to the product of the supply width d of the aqueous cobalt salt solution and the flow velocity v of the suspension, that is, $D/\{\rho/(d \times v)\}$ was $0.335 \times 10^5$ cm$^3$/mol. It is to be noted that the temperature of the suspension during reaction was controlled to be 50° C.

Figure 5:
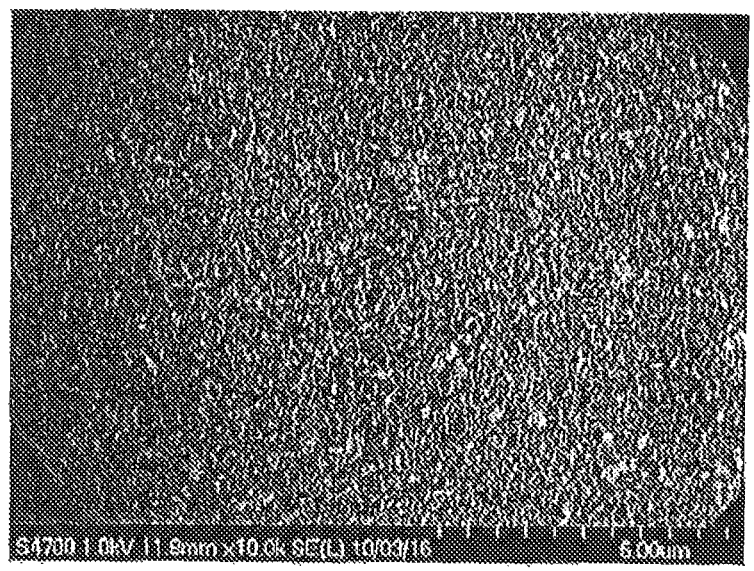
FIG. 5 A scanning electron micrograph of a cobalt oxyhydroxide-coated nickel hydroxide powder prepared in Comparative Example 1.

The obtained cobalt oxyhydroxide-coated nickel hydroxide powder was dark brown. The powder was observed with a SEM to evaluate the state of the cobalt oxyhydroxide coating. As a result, as shown in FIG. 5, cobalt oxyhydroxide scales were observed in some positions on the surface of the nickel hydroxide particles; therefore, the nickel hydroxide particles were found to be non-uniformly coated.

Transmittances A, $B_0$, and $B_{max}$ were determined in the same manner as in Example 1, and the transmittance ratio (%) of the cobalt oxyhydroxide-coated nickel hydroxide powder was calculated using the formula $(A-B_{max})/(B_0-B_{max}) \times 100$. As a result, the transmittance ratio was 25.6%.

Comparative Example 2

A cobalt oxyhydroxide-coated nickel hydroxide powder was obtained in the same manner as in Example 2 except that the aqueous cobalt sulfate solution was added using a roller pump in 2 hours at an addition rate of 672.4 ml/min from one supply port having a diameter of 8 mm. Further, cobalt hydroxide deposited on the surface of nickel hydroxide particles was oxidized in the same manner as in Example 1 to obtain a cobalt oxyhydroxide-coated nickel hydroxide powder.

At this time, the ratio of the supply rate ρ of the aqueous cobalt salt solution to the product of the supply width d of the aqueous cobalt salt solution supplied to the suspension and the flow velocity v of the suspension, that is, $\rho/(d \times v)$ was $4.51 \times 10^{-4}$ mol/cm$^2$. The ratio of the distance D between the supply position of the aqueous cobalt salt solution and the supply position of the aqueous alkali solution to the ratio of the supply rate ρ of the aqueous cobalt salt solution to the product of the supply width d of the aqueous cobalt salt solution and the flow velocity v of the suspension, that is, $D/\{\rho/(d \times v)\}$ was $0.443 \times 10$ cm$^3$/mol. It is to be noted that the temperature of the suspension during reaction was controlled to be 50° C.

The obtained cobalt oxyhydroxide-coated nickel hydroxide powder was dark brown. The powder was observed with a SEM to evaluate the state of the cobalt oxyhydroxide coating. As a result, as in the case of Comparative Example 1, cobalt oxyhydroxide scales were observed in some positions on the surface of the nickel hydroxide particles; therefore, the nickel hydroxide particles were found to be non-uniformly coated.

Transmittances A, $B_0$, and $B_{max}$ were determined in the same manner as in Example 1, and the transmittance ratio (%) of the cobalt oxyhydroxide-coated nickel hydroxide powder was calculated using the formula $(A-B_{max})/(B_0-B_{max}) \times 100$. As a result, the transmittance ratio was 19.7%, As can be seen from the above Examples and Comparative Examples, the coated nickel hydroxide powders of Examples prepared at a ratio $\rho/(d \times v)$ of $3.5 \times 10^{-4}$ mol/cm$^2$ or less and a ratio $D/\{\rho/(d \times v)\}$ of $0.5 \times 10^5$ cm$^3$/mol or more have a uniform coating on the surface of particles thereof and are excellent in coating adhesion properties. On the other hand, the coated nickel hydroxide powders of the Comparative Examples prepared at a ratio $\rho/(d \times v)$ of more than $3.5 \times 10^{-4}$ mol/cm$^2$ and a ratio $D/\{\rho/(d \times v)\}$ of less than $0.5 \times 10^5$ cm$^3$/mol are poor in coating adhesion properties.

Further, each of the coated nickel hydroxide powders after shaking was turned into slurry to separate the coated nickel hydroxide powder from the coating peeled off, and the pressed powder resistance of the coated nickel hydroxide powder was measured. As a result, the coated nickel hydroxide powders of Examples were found to have higher conductivity than the coated nickel hydroxide powders of Comparative Examples. This shows that the coated nickel hydroxide powders of Examples are suitable for a positive electrode active material of alkaline secondary battery.

INDUSTRIAL APPLICABILITY

The coated nickel hydroxide powder according to the present invention has high conductivity; therefore, its utilization ratio as a positive electrode active material is high. Therefore, the coated nickel hydroxide powder according to the present invention is suitable for use in a power source for portable electronic device required to have a high capacity. Further, the coated nickel hydroxide powder according to the present invention is suitable for use in a power source for electric car or hybrid car required to have high-output characteristics.

REFERENCE SIGNS LIST

1 Tubular transparent cell

The invention claimed is:
1. A coated nickel hydroxide powder for a positive electrode active material of alkaline secondary battery, comprising nickel hydroxide particles having a coating made of a cobalt compound on a surface thereof,
   wherein the nickel hydroxide particles used as a core material to be coated with the cobalt compound have a composition represented by the general formula $Ni_{1-x-y}Co_xM_y(OH)_2$, wherein x is 0.005 to 0.05, y is 0.005 to 0.05, and M is at least one element selected from Ca, Mg, and Zn,
   wherein said nickel hydroxide particles having the coating made of the cobalt compound on a surface thereof are obtained by a crystallization reaction in which a nickel hydroxide powder is dispersed in water to prepare a suspension, and then an aqueous cobalt salt solution and an aqueous alkali solution are supplied to the stirred suspension while keeping a pH of the suspension mixed with the aqueous cobalt salt solution and the aqueous alkali solution in a range from 8 to 11.5 as measured at 25° C., and thereafter cobalt hydroxide that coats the surface of the nickel hydroxide particles is oxidized while stirring the suspension, such that the cobalt compound constituting the coating mainly contains cobalt oxyhydroxide or a mixture of cobalt oxyhydroxide and cobalt hydroxide, and an amount of cobalt contained in the cobalt compound constituting the coating is 90 mass % or more with respect to a total mass of metal elements contained in the coating,
   wherein when a transmittance A, a transmittance $B_0$, and a transmittance $B_{max}$ are defined as follows, a transmittance ratio (%) represented by $(A-B_{max})/(B_0-B_{max}) \times 100$ is 30% or higher,
   transmittance A: transmittance of a tubular transparent cell measured after shaking the tubular transparent cell containing the coated nickel hydroxide powder for a predetermined time and then taking the contents out of the tubular transparent cell;
   transmittance $B_0$: transmittance of a tubular transparent cell measured after shaking the tubular transparent cell containing a nickel hydroxide powder for a predetermined time and then taking the contents out of the tubular transparent cell; and transmittance $B_{max}$: transmittance of a tubular transparent cell measured after shaking the tubular transparent cell, for a predetermined time, containing the nickel hydroxide powder and a cobalt compound powder containing cobalt in an amount corresponding to an amount of cobalt contained in the coating of the coated nickel hydroxide powder and then taking the contents out of the tubular transparent cell.

2. The coated nickel hydroxide powder for a positive electrode active material of alkaline secondary battery according to claim 1, wherein an amount of cobalt contained in the cobalt compound constituting the coating is 1 to 10 mass % with respect to a total mass of the coated nickel hydroxide powder.

3. An evaluation method for coating adhesion properties of a coated nickel hydroxide powder for a positive electrode active material of alkaline secondary battery comprising nickel hydroxide particles having a coating made of a cobalt compound on a surface thereof, the method comprising: measuring transmittances A, $B_0$, and $B_{max}$ defined as follows; and evaluating coating adhesion properties of a coated nickel hydroxide powder based on a transmittance ratio (%) represented by $(A-B_{max})/(B_0-B_{max})\times 100$, transmittance A: transmittance of a tubular transparent cell measured after shaking the tubular transparent cell containing the coated nickel hydroxide powder for a predetermined time and then taking the contents out of the tubular transparent cell;

transmittance $B_0$: transmittance of a tubular transparent cell measured after shaking the tubular transparent cell containing a nickel hydroxide powder for a predetermined time and then taking the contents out of the tubular transparent cell; and transmittance $B_{max}$: transmittance of a tubular transparent cell measured after shaking the tubular transparent cell, for a predetermined time, containing the nickel hydroxide powder and a cobalt compound powder containing cobalt in an amount corresponding to an amount of cobalt contained in the coating of the coated nickel hydroxide powder and then taking the contents out of the tubular transparent cell.

4. The evaluation method for coating adhesion properties of a coated nickel hydroxide powder according to claim 3, wherein the tubular transparent cell is a circular or rectangular cylindrical transparent cell.

5. The evaluation method for coating adhesion properties of a coated nickel hydroxide powder according to claim 4, wherein the tubular transparent cell is a transparent cell made of quartz or glass.

6. The evaluation method for coating adhesion properties of a coated nickel hydroxide powder according to claim 5, wherein the shaking of the tubular transparent cell is performed by performing reciprocating movement in a direction parallel to a central axis of the cell or by performing the reciprocating movement simultaneously with rotational or semi-rotational movement around the central axis of the cell.

7. The evaluation method for coating adhesion properties of a coated nickel hydroxide powder according to claim 4, wherein the shaking of the tubular transparent cell is performed by performing reciprocating movement in a direction parallel to a central axis of the cell or by performing the reciprocating movement simultaneously with rotational or semi-rotational movement around the central axis of the cell.

8. The evaluation method for coating adhesion properties of a coated nickel hydroxide powder according to claim 4, wherein a time of shaking the tubular transparent cell is a total time of shaking performed until a reduction rate of the transmittance A per minute (%/min) determined by measuring the transmittance A every ten-minute shaking becomes 0.3% or less of an initial transmittance.

9. The evaluation method for coating adhesion properties of a coated nickel hydroxide powder according to claim 3, wherein the tubular transparent cell is a transparent cell made of quartz or glass.

10. The evaluation method for coating adhesion properties of a coated nickel hydroxide powder according to claim 9, wherein the shaking of the tubular transparent cell is performed by performing reciprocating movement in a direction parallel to a central axis of the cell or by performing the reciprocating movement simultaneously with rotational or semi-rotational movement around the central axis of the cell.

11. The evaluation method for coating adhesion properties of a coated nickel hydroxide powder according to claim 9, wherein a time of shaking the tubular transparent cell is a total time of shaking performed until a reduction rate of the transmittance A per minute (%/min) determined by measuring the transmittance A every ten-minute shaking becomes 0.3% or less of an initial transmittance.

12. The evaluation method for coating adhesion properties of a coated nickel hydroxide powder according to claim 3, wherein the shaking of the tubular transparent cell is performed by performing reciprocating movement in a direction parallel to a central axis of the cell or by performing the reciprocating movement simultaneously with rotational or semi-rotational movement around the central axis of the cell.

13. The evaluation method for coating adhesion properties of a coated nickel hydroxide powder according to claim 12, wherein a time of shaking the tubular transparent cell is a total time of shaking performed until a reduction rate of the transmittance A per minute (%/min) determined by measuring the transmittance A every ten-minute shaking becomes 0.3% or less of an initial transmittance.

14. The evaluation method for coating adhesion properties of a coated nickel hydroxide powder according to claim 3, wherein a time of shaking the tubular transparent cell is a total time of shaking performed until a reduction rate of the transmittance A per minute (%/min) determined by measuring the transmittance A every ten-minute shaking becomes 0.3% or less of an initial transmittance.

\* \* \* \* \*